United States Patent
Suzuki et al.

(10) Patent No.: US 8,741,328 B2
(45) Date of Patent: Jun. 3, 2014

(54) NERVE REGENERATION-INDUCING TUBE

(75) Inventors: Michiko Suzuki, Ohtsu (JP); Fumihiko Kajii, Ohtsu (JP); Hidenori Tanaka, Ohtsu (JP); Susumu Kashiwabara, Ohtsu (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 147 days.

(21) Appl. No.: 13/147,234

(22) PCT Filed: Feb. 2, 2009

(86) PCT No.: PCT/JP2009/051702
§ 371 (c)(1),
(2), (4) Date: Aug. 1, 2011

(87) PCT Pub. No.: WO2010/087015
PCT Pub. Date: Aug. 5, 2010

(65) Prior Publication Data
US 2011/0288569 A1    Nov. 24, 2011

(51) Int. Cl.
*A61F 2/04*    (2013.01)
*A61K 33/14*    (2006.01)

(52) U.S. Cl.
USPC ....... 424/426; 424/680; 623/1.47; 623/23.64; 623/23.75

(58) Field of Classification Search
CPC .................. A61K 33/14; A61F 2/04
See application file for complete search history.

(56) References Cited

U.S. PATENT DOCUMENTS

| | | | |
|---|---|---|---|
| 4,863,668 A * | 9/1989 | Griffiths et al. | 264/512 |
| 4,975,527 A | 12/1990 | Koezuka et al. | |
| 6,090,117 A | 7/2000 | Shimizu | |
| 6,589,257 B1 | 7/2003 | Shimizu | |
| 2007/0232787 A1 * | 10/2007 | Kobayashi et al. | 530/356 |

FOREIGN PATENT DOCUMENTS

| | | |
|---|---|---|
| CN | 1629191 A | 6/2005 |
| CN | 1891179 A | 1/2007 |
| JP | 5-237139 A | 9/1993 |
| JP | 08-283666 A | 10/1996 |
| JP | 08-283667 A | 10/1996 |
| JP | 2000-325463 A | 11/2000 |
| JP | 2001-070436 A | 3/2001 |
| JP | 2002-320630 A | 11/2002 |
| JP | 2003-019196 A | 1/2003 |
| JP | 2003-301362 A | 10/2003 |
| JP | 2004-149455 A | 5/2004 |

(Continued)

OTHER PUBLICATIONS

Nakada et al. ( Biomed Mater. 2013, 8, 1-9).*

(Continued)

*Primary Examiner* — Ernst Arnold
(74) *Attorney, Agent, or Firm* — Westerman, Hattori, Daniels & Adrian, LLP

(57) ABSTRACT

The present invention provides a nerve regeneration-inducing tube in which collagen having excellent adhesive property, cell growth property and differentiation inducing property to nerve cells is used as a scaffold for the nerve regeneration. The nerve regeneration-inducing tube is characterized in using the collagen which is made the concentration of sodium chloride contained therein not more than 2.0% by weight or, preferably, 0.1 to 1.5% by weight in a dry state. Purification of collagen is carried out by means of an isoelectric precipitation where the pH is 6.0 or higher and is lower than 10.0.

4 Claims, 8 Drawing Sheets

(56) References Cited

FOREIGN PATENT DOCUMENTS

| | | | |
|---|---|---|---|
| JP | 2005-343853 A | 12/2005 | |
| JP | 2007-159866 A | 6/2007 | |
| JP | 2009-34374 A | 2/2009 | |
| WO | 98/22155 A1 | 5/1998 | |
| WO | 99/63908 A1 | 12/1999 | |
| WO | WO 0247557 * | 6/2002 | ............ A61B 17/11 |
| WO | 2009/017224 A1 | 2/2009 | |

OTHER PUBLICATIONS

International Search Report for PCT/JP2009/051702, mailing date of Mar. 3, 2009.

Extended European Search Report dated Dec. 20, 2012, issued in corresponding European Search Report 09839205.3, (7 pages).

Office Action dated Oct. 10, 2012, cited in Chinese application No. 200980158621.X, with English Translation.

\* cited by examiner

Fig. 1
State of the cells in the collagen gel of the inventive examples after incubating for four days
(1)
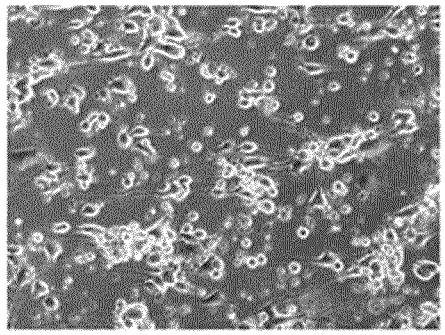
Cells grow and neurites elongate
(2)
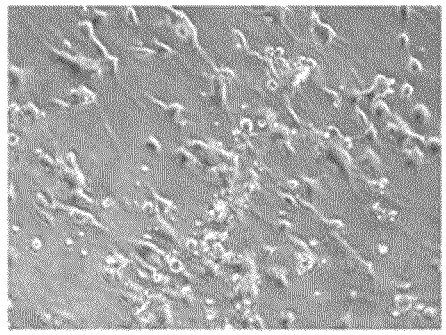
Neurites elongate in a certain direction
(3)
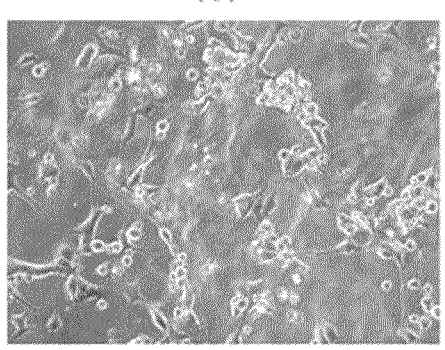
Neurites elongate in three dimensions
(4)
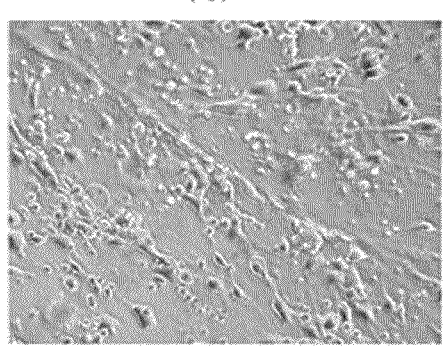
Cells and neurites elongate in a certain direction Fig. 2
State of the cells in the collagen gel of the comparative examples after incubating for four days
(1)
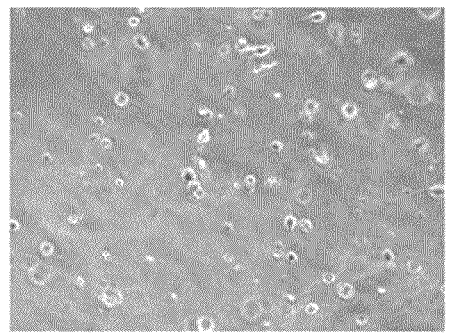
Cells do not grow well, and almost no neurite exists
(2)
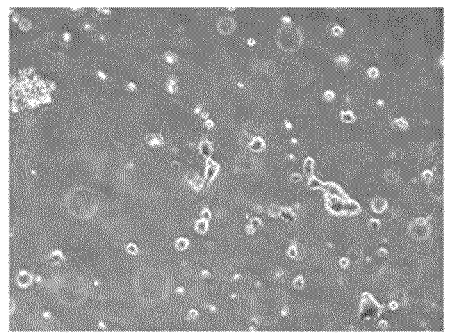
Cells do not grow well, and almost no neurite exists
(3)
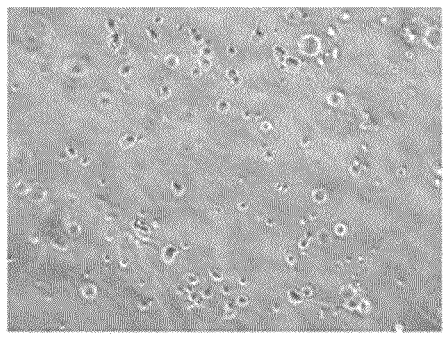
Cells do not grow well, and almost no neurite exists

Fig. 5

|  | Type of the collagen | Concentration of sodium chloride |
|---|---|---|
| Collagen coat 1 | Collagen of the inventive examples | 1% |
| Collagen coat 2 | Collagen of the inventive examples | 5% |
| Collagen coat 3 | Collagen of the inventive examples | 10% |
| Collagen coat 4 | Collagen of the comparative examples | 4% |
| Collagen coat 5 | Collagen of the comparative examples | 5% |
| Collagen coat 6 | Collagen of the comparative examples | 10% |

Fig. 6

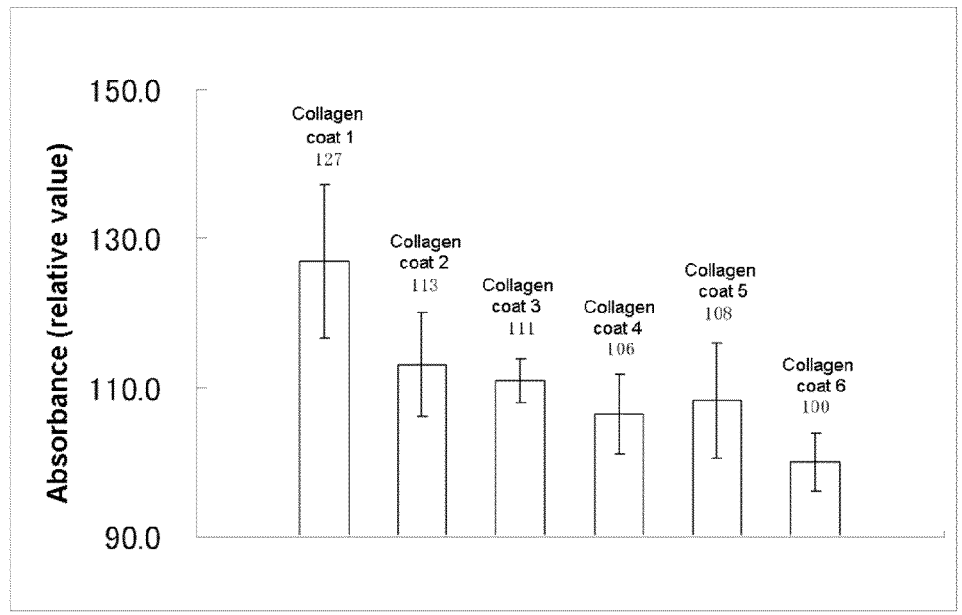

NERVE REGENERATION-INDUCING TUBE

TECHNICAL FIELD OF THE INVENTION

The present invention relates to a nerve regeneration-inducing tube by which peripheral nerve cut or excised by accident or surgical operation is reconnected utilizing the elongation of nerve cells. More particularly, the present invention relates to a nerve regeneration-inducing tube wherein collagen is used as a scaffold for nerve regeneration, and wherein nerve tissues cut or excised are fixed at their extended direction and are connected to each other without being inhibited by surrounding tissues.

BACKGROUND ART

There are many examples where damage of peripheral nerve caused by accident or the like cannot be completely restored. There are also many clinical examples where peripheral nerve must be excised as a result of surgical operations in general. In the damage of peripheral nerves, autologous nerve grafting has been an only means besides a direct anastomosis. However, the result thereof is not always satisfactory but recovery of sensory perception and capacity for locomotion are bad and the aftereffect due to erroneous governing is noted as well. In addition, there are many patients complaining not only the aftereffect such as pain and deficiency in sensory perception but also the abnormal sensory perception of the diseased area or, particularly, pain.

An attempt for the regeneration of nerve by connection of gaps of peripheral nerve using a connecting tube made of artificial materials has been briskly carried out since early 1980's. However, all of the studies of connecting channels using non-absorptive synthetic artificial materials have resulted in failure. In order to solve the above, it is necessary to consider in the followings such as that invasion of connective tissues from outside is prevented during the regeneration of nerve bundles, that substance interchange inside and outside the channels or neogenesis of capillary blood vessels in channel walls is necessary, that a substance acting as a scaffold suitable for the growth of Schwann cells and axon in the channel is necessary and that, after the regeneration, the used material is degraded and absorbed. Taking those conditions into consideration, studies for artificial nerve connecting tube by a biodegradable and bioabsorbable material have been carried out thereafter.

With regard to the regeneration of peripheral nerve, attempts for extending the distance between the stumps which can be regenerated using a silicone tube have been conducted since a silicone tube model was reported in 1982. However, since nutrients cannot permeate through the wall of silicone tube, there is a problem such as that the nutrients are not sufficiently provided to nerve axon whereby capillary blood vessel cannot be produced in silicone and no satisfactory nerve regeneration has been available even when a silicone tube is used. Further, even if the nerve can be regenerated, there is a problem that the silicone tube which is a foreign substance anyway must be removed by means of further surgical operation, etc.

On the other hand, regeneration of peripheral nerve using a tube comprising a biodegradable polymer in place of a silicone tube has been attempted. When a nerve regeneration tube comprising a biodegradable polymer is used, the nerve regeneration tube is gradually degraded and absorbed in vivo by hydrolysis or by the action of enzymes after the nerve is regenerated whereby there is no need of taking out it by a means such as further surgical operation.

With regard to a nerve regeneration tube comprising a biodegradable polymer as such, there is a disclosure in, for example the Patent Document 1, for an auxiliary material for nerve regeneration which comprises bundles of collagen fiber on which laminin and fibronectin are coated. In the Patent Document 2, there is a disclosure for a tube which comprises biodegradable and bioabsorbable materials and, in the lumen of the tube, a collagen body having gaps and penetrating the tube nearly in parallel to the axial line of said tube where the gap is filled with a matrix gel containing collagen, laminin, etc. In the Patent Document 3, there is a disclosure for an artificial nerve tube which comprises a tube comprising biodegradable and bioabsorbable materials and laminin-coated collagen fiber bundles inserted into the lumen of the tube nearly in parallel to the axial line of the tube. In the Patent Document 4, there is a disclosure for a substrate material for the reconstruction of nerves having a structure where fibers comprising a bioabsorbable material are bundled. In the Patent Document 5, there is a disclosure for a support such as sponge, tube or coil comprising collagen. In the Patent Document 6, there is a disclosure for a support which is composed of a spongy fine matrix comprising a biodegradable material or a bioabsorbable material and a linear biotissue induction path or a linear organ induction path. In the Patent Document 7, there is a disclosure for a nerve regeneration tube containing a sponge comprising a biodegradable polymer material and a reinforcing material comprising a biodegradable polymer having longer period for degradation and absorption than that of said sponge wherein the inner side thereof comprises sponge.

All of those nerve regeneration tubes use collagen as a scaffold for nerve regeneration but their adhesive property, cell growth property and differentiation inducing property of collagen to nerve cells are not satisfactory.

Patent Document 1: Japanese Patent Application Laid-Open (JP-A) No. 237139/93
Patent Document 2: WO 98/22155
Patent Document 3: WO 99/63908
Patent Document 4: Japanese Patent Application Laid-Open (JP-A) No. 2000-325463
Patent Document 5: Japanese Patent Application Laid-Open (JP-A) No. 2001-70436
Patent Document 6: Japanese Patent Application Laid-Open (JP-A) No. 2002-320630
Patent Document 7: Japanese Patent Application Laid-Open (JP-A) No. 2003-19196

DISCLOSURE OF THE INVENTION

Problem that the Invention is to Solve

The present invention has been devised in view of the current status of the prior art as such and its object is to provide a nerve regeneration-inducing tube in which collagen having excellent adhesive property, cell growth property and differentiation inducing property to nerve cells is used as a scaffold for the nerve regeneration.

Means for Solving the Problem

In order to achieve such an object, the present inventor has investigated for a method of producing the collagen which is used as a scaffold of nerve regeneration and, as a result, the present inventor has found that sodium chloride which is inevitably contaminated in the stages of washing and salting-out during the production of collagen from materials such as pigskin badly affect the regeneration of nerve cells and that, when collagen where the sodium chloride concentration is lowered is used, growth of nerve cells and elongation of neurite are enhanced whereupon the present invention has been accomplished.

Thus, the present invention relates, in a nerve regeneration-inducing tube where collagen is used as a scaffold for nerve regeneration, to a nerve regeneration-inducing tube which is characterized in using the collagen which is purified so as to make the concentration of sodium chloride contained therein not more than 2.0% by weight or, preferably, 0.1 to 1.5% by weight in a dry state.

In a preferred embodiment of the nerve regeneration inducing tube of the present invention, purification of collagen is carried out by means of an isoelectric precipitation where the pH is 6.0 or higher and is lower than 10.0, the nerve regeneration-inducing tube is formed by coating the collagen on a tubular body comprising a biodegradable polymer and filling the collagen into the tubular body, the biodegradable polymer is selected from the group consisting of polyglycolic acid, polylactic acid and a copolymer of lactic acid with caprolactone and the tubular body has an inner diameter of 0.1 to 20 mm, an outer diameter of 0.15 to 25 mm and a length of 1.0 to 150 mm.

Advantages of the Invention

In accordance with the present invention, there is used pure collagen where the concentration of sodium chloride which is inevitably contaminated during the producing steps for collagen is lowered to not more than 2% by weigh whereby it is now possible to provide a nerve regeneration-inducing tube having excellent adhesive property, cell growth property and differentiation inducing property to nerve cells.

BRIEF DESCRIPTION OF THE DRAWINGS

FIG. 1 is a microscopic picture showing the state of cells in collagen gel in the inventive example.

FIG. 2 is a microscopic picture showing the state of cells in collagen gel in the comparative example.

FIG. 5 shows the details of the collagen coats 1 to 6 used in Experiment 3.

FIG. 6 is a graph of absorption (relative values) measured in Experiment 3.

BEST MODE FOR CARRYING OUT THE INVENTION

Figure 3:
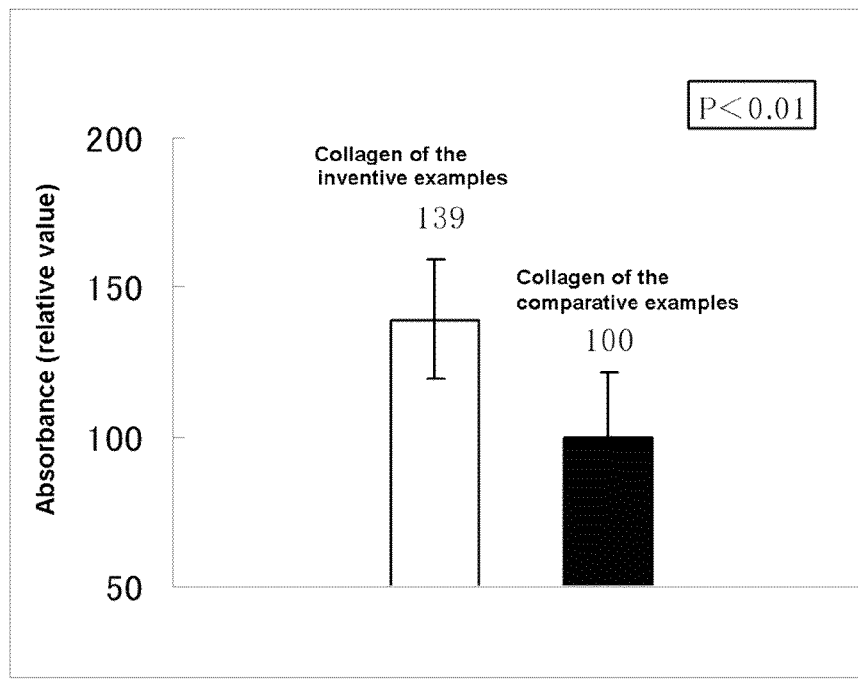
FIG. 3 is a graph of absorption (relative values) measured in Experiment 1.

The nerve regeneration-inducing tube of the present invention is characterized in using the collagen which is purified so as to make the concentration of sodium chloride contaminated therein during the production steps for collagen not more than 2% by weight in a dry state as a scaffold for nerve regeneration.

Since collagen plays a role of a substrate for various kinds of cells, its affinity to the tissues is good when applied to living bodies as a medical material whereby it has been used already as a scaffold for the growth of nerve cells.

The conventional collagen used as a scaffold for the nerve regeneration is usually prepared by the following manner. Thus, the pigskin collected and frozen in a meat testing factory is used as a starting material, a neutral protease is added thereto followed by warming, repeatedly washed with a sodium chloride solution, dehydrated, washed with isopropanol and acetone and dried in vacuo, the resulting defatted chip is added to an acetic acid solution, the pH is adjusted using hydrochloric acid, pepsin is added thereto to decompose, a sodium hydroxide solution is added to adjust to high pH (a virus inactivating step 1), hydrochloric acid is added to adjust to low pH (a virus inactivating step 2), the pH is adjusted to 2 to 3 using sodium hydroxide followed by filtering, a sodium chloride solution is added to the filtrate to salt out, a concentrating operation is conducted by means of centrifugal separation, the concentrated product is added to and dissolved in pure water, a sodium chloride solution is added thereto once again to salt out and the mixture is concentrated by means of centrifugal separation followed by freeze-drying.

The conventionally used collagen as such includes the steps of washing with a sodium chloride solution and salting-out using a sodium chloride solution during its manufacturing process whereby the concentration of sodium chloride in the collagen, including that which is available in the market, is 4% by weight or more. The present inventors thought that the sodium chloride concentration in the collagen affects the living and the growth of nerve cells and that, when the concentration is too high, cell membrane is destroyed due to osmotic pressure. Therefore, when collagen which is purified so as to reduce the concentration of sodium chloride contained therein is used for a nerve regeneration-inducing tube, the resulting nerve regeneration-inducing tube achieves far better cell adhesive property and cell growth property than the one which uses the conventional collagen. On the basis of the finding as such, the present invention uses pure collagen where the concentration of sodium chloride in terms of a dry state contained therein is reduced to 2.0% by weight or less, preferably 0.1 to 1.5% by weight as a scaffold of the nerve regeneration-inducing tube. The concentration of sodium chloride is measured by means of atomic absorption spectrophotometry (by making into ash). For a purpose of prevention of destruction of cell membrane by lowering of osmotic pressure, the lower the sodium chloride concentration, the better. However, in view of technical standpoint and stability of collagen, about 0.1% by weight will be the lower limit. As a method for lowering the salt concentration, there are isoelectric precipitation (concentration) method as described hereinafter, dialysis method and so on. In the present invention, any known method can be used.

Measurement of sodium chloride concentration by means of atomic absorption spectrophotometry is carried out by such a manner that 1 to 4 g of a sample is taken into a quartz beaker, carbonized by a gradual rise of temperature on an electric heater and finally made into ash by treating in a Muffle furnace for 6 to 8 hours (500° C.), and the residue is re-dissolved in a 10 wt % aqueous solution of hydrochloric acid and diluted so as to make the final concentration 1 wt % and then the measurement is conducted by means of a flame atomic absorption spectrophotometry using acetylene and air. The measuring wavelength is 589.6 nm.

Collagen used in the nerve regeneration-inducing tube of the present invention may be produced by any of the conventionally known methods and, for example, it can be produced by such a manner where the conventional collagen which has been available in the market for medical use as mentioned above is used as a starting material, dissolved in distilled water for injection under cooling at 2 to 10° C., subjected to pH adjustment within a range of from 6.0 to lower than 10.0 using a sodium hydroxide solution, subjected to an isoelectric precipitation and centrifuged, the supernatant liquid is discarded and the precipitate is freeze-dried. The present inventors found that extremely superior cell differentiation inducing property can be exhibited by using collagen having such an isoelectric point range, whereby the present invention is completed. Although a detailed reason why the cell differentiation inducing property is enhanced by the use of collagen having an isoelectric point of from 6.0 to lower than 10.0 as a scaffold for the nerve regeneration is not clear, there is a possibility that the fraction precipitated when pH is lower than 6.0 and 10.0 or higher contains a factor having low affinity to cells and, on the contrary, it is also likely that the collagen precipitated when pH is from 6.0 to lower than 10.0 has a particularly high affinity to cells. Alternatively, the unpurified collagen is constituted from type I collagen and type III collagen in a ratio of about 7:3 and there may be an influence by changing this constituting ratio of type I to type III. In the present invention, range of isoelectric point is more preferably from pH 7.0 to lower than 9.5 and more preferably from pH 8.0 to lower than 9.0.

The nerve regeneration-inducing tube of the present invention can be manufactured by the conventionally known methods and, for example, it can be formed by such a manner that collagen is coated on a tubular body comprising biodegradable polymer and then the collagen is filled in the inner area of the tubular body. Although the size of the tubular body may vary depending upon the site of the nerve to be regenerated and also upon the strength necessary therefor, it is usual that an inner diameter is 0.1 to 20 mm, an outer diameter is 0.15 to 25 mm and a length is 1.0 to 150 mm. Actually, it is preferred to previously prepare the nerve regeneration-inducing tubes comprising tubular bodies in various sizes in view of the time restriction and the production cost.

Examples of the biodegradable polymer constituting the tubular body include polyglycolic acid, polylactic acid, a lactic acid-caprolactone copolymer, a glycolic acid-caprolactone copolymer, polydioxanone and glycolic acid-trimethylenecarboxylic acid. In view of easy availability and handling, it is preferred to use polyglycolic acid, polylactic acid or a lactic acid-caprolactone copolymer and it is particularly preferred to use polyglycolic acid. Each of those biodegradable polymers may be used solely or two or more thereof may be used by mixing.

As to the tubular body, there may be used a body where the above-mentioned biodegradable polymer is made into porous tubular body or a body where plural ultrafine fibers of the above-mentioned biodegradable polymer are bundled followed by weaving into a tubular shape. Pore size and void fraction of the porous thing and the stitch (meshes) may be appropriately adjusted depending upon the aimed use and strength.

Diameter of the ultrafine fiber comprising the biodegradable polymer is preferred to be from 1 to 50 µm. When the fiber diameter is too small, the fiber gap becomes dense whereby it may happen that collagen is hardly permeated into the tubular body or that flexibility of the tubular body lowers. On the contrary, when the fiber diameter is too large, the retained amount of collagen becomes small whereby it may happen that the growing speed of the nerve does not rise or that the strength of the tubular body becomes insufficient. More preferably, diameter of the ultrafine fiber is 3 to 40 µm, and further preferably 6 to 30 µm.

In the formation of the tubular body, it is preferred that 5 to 60 of the ultrafine fibers comprising the biodegradable polymer and having the above fiber diameter are bundled and alternately knitted as warps and woofs. When the numbers of the ultrafine fibers to be bundled are too small, it may happen that the strength of the tubular body becomes insufficient or that a sufficient retained-amount of collagen cannot be secured. On the contrary, when the numbers of the ultrafine fibers to be bundled are too many, it may happen that a tubular body in fine diameter cannot be prepared or that flexibility of the tubular body cannot be secured. More preferably, the numbers of the ultrafine fibers are 10 to 50, and further preferably 20 to 40.

When a tubular body is formed by an alternate knitting of the ultrafine fiber bundles, the pore size of the network is preferred to be about 5 to 300 µm, and more preferably 10 to 200 µm. When the pore size of the network is too small, it may happen that growth of the cells and the tissues is inhibited due to the lowering of invasion of capillary blood vessel or due to the lowering of water permeability. When it is more than about 300 µm, invasion of the tissues becomes excessive whereby growth of the cells and the tissues may be inhibited.

In the present invention, the outer surface of the tubular body is coated by applying a collagen solution for several times by a method which has been known among persons skilled in the art while the inner area (lumen) of the tubular body is filled by charging collagen therein. The collagen solution used therein may contain laminin, heparan sulfate proteoglycan, entactin and growth factor. Examples of the growth factor include EGF (epidermal growth factor), PFGF (fibroblast growth factor), NGF (nerve growth factor), PDGF (platelet-derived growth factor), IGF-1 (insulin-like growth factor) and TGF-β (transforming growth factor). With regard to the collagen solution, it is preferred that, after every one application thereof in a form of a solution in hydrochloric acid using a brush or a writing brush, the solution is completely dried and then the next application is conducted whereby a plurality of applications are done.

It is preferred that the tubular body where collagen is coated or filled is subjected to freezing, freeze-drying and cross-linking treatments to cross-link the collagen. The freezing is carried out under the condition of preferably −10 to −196° C. and more preferably −20 to −80° C. for 3 to 48 hours. As a result of the freezing, fine ice is formed among the collagen molecules and the collagen solution results in a phase separation to give sponge. After that, the above frozen collagen solution is freeze-dried in vacuo at about −40 to −80° C. of initial temperature and for about 12 to 48 hours. As a result of freeze-drying, fine ice among the collagen molecules is evaporated and, at the same time, the collagen sponge becomes fine. Examples of the cross-linking method include γ-ray cross-linking, ultraviolet cross-linking, electronic ray cross-linking, thermal dehydration cross-linking, glutaraldehyde cross-linking, epoxy cross-linking and water-soluble carbodiimide cross-linking and, among them, a thermal dehydration cross-linking where the cross-linking degree can be easily controlled and living body is not effected even by conducting the cross-linking treatment is preferred. The thermal dehydration cross-linking is conducted in vacuo at, for example, about 105 to 150° C., more preferably about 120 to 150° C., and further preferably about 140° C. for about 6 to 24 hours, more preferably about 6 to 12 hours, and further preferably about 12 hours. When the cross-linking temperature is too high, there is a possibility that the strength of the biodegradable and bioabsorbable material lowers while, when it is too low, there is a possibility that no sufficient cross-linking reaction takes place.

EXAMPLES

Experiments which actually prove the superiority of the collagen of the present invention will be shown below.

(Measurement of the Concentration of Sodium Chloride)

Measurement of the concentration of sodium chloride by atomic absorption spectrometry is conducted in such a manner that 1 to 4 g of a sample is placed in a quartz beaker, carbonized on an electric heater by gradually raising the temperature and, finally, made into ash in a muffle furnace for 6 to 8 hours (500° C.). The residue is re-dissolved in a 10 wt % aqueous solution of hydrochloric acid, diluted so as to make the final concentration 1% by weight and subjected to the measurement by means of a flame atomic absorption method using acetylene-air. Incidentally, the measuring wavelength is 589.6 nm.

Experiment 1: Experiment for the incubation of collagen gel

1. Object of this Experiment

Usually, a two-dimensional incubation on the bottom of a well-plate is fundamental in the cell incubation experiments. However, it has been said that, when a three-dimensional incubation is conducted, behavior of the cells is greatly different from that in the case of the two-dimensional incubation and, in evaluating the nerve regeneration, it has been believed that the three-dimensional incubation is a system which is nearer the actual system. Accordingly, in this experiment, a three-dimensional incubation is carried out using collagen gel for a purpose of confirming whether the behavior of the incubated cells is different depending upon the type of the collagen.

2. Collagen Used in this Experiment (1) Collagen for the Comparative Examples

"NMP Collagen PS" manufactured by Nippon Ham was used as a collagen for the comparative examples. This collagen for the comparative examples is manufactured by such a manner that pigskin is used as a starting material and is subjected to the defatting and purifying treatments. The defatting treatment includes the repeated washing steps using a sodium chloride solution while the purifying treatment includes a salting-out step using sodium chloride. When this collagen for the comparative examples was measured by means of an atomic absorption spectrometry (by making into ash), it contained 4.0% by weight of sodium chloride in its dry state.

(2) Collagen of the Inventive Examples

A part of the above collagen for the comparative examples was used as a starting material and was purified by means of an isoelectric precipitation where pH was 8 or higher and lower than 9 whereupon the collagen of the inventive examples was prepared. When this collagen of the inventive examples was measured by means of an atomic absorption spectrometry (by making into ash), it contained 1.0% by weight of sodium chloride in its dry state.

3. Preparation of Collagen Gel Medium

Each of the above-prepared two kinds of collagen was dissolved in hydrochloric acid according to the conventional method to prepare a 0.5 wt % solution of collagen in hydrochloric acid. Each 300 µl of the collagen solution of the inventive examples among the above was added to eight wells of a 24-well microplate (manufactured by Iwaki) while each 300 µl of the collagen solution of the comparative examples was added to other eight wells of the same plate. After that, the plate was allowed to stand at 37° C. in an incubator for 30 minutes.

4. Collagen Gel Incubation of the PC12 Cells (1) PC12 cells (cells derived from the adrenal pheochromocytoma of rats manufactured by Dainippon Pharmaceutical Laboratory Products) were previously cultured on a DMEM medium until six passage numbers, the cells were recovered by centrifugal separation and suspended in 15 ml of the DMEM medium so as to adjust the cell numbers to $1 \times 10^6$ cells and then 15 µl of a 50 µg/ml NGF (cell growth factor manufactured by R&D Systems Inc.; a phosphate buffer) was added thereto whereupon a culture solution was prepared.

Incidentally, the DMEM medium is such a one where 25 ml of fetal bovine serum (manufactured by Dainippon Pharmaceutical Laboratory Products), 50 ml of equine serum (manufactured by Dainippon Pharmaceutical Laboratory Products) and 5 ml of 200 mM glutamine solution (manufactured by Dainippon Pharmaceutical Laboratory Products; 29.23 mg/ml) are added to and mixed with 500 ml of an RPMI 1640 liquid medium (manufactured by Dainippon Pharmaceutical Laboratory Products; containing no glutamic acid and containing sodium bicarbonate).

(2) Each 300 µl of the culture solution prepared as such was dropped into the well of the previously-prepared collagen medium.

(3) The well plate was incubated in an incubator (37° C.; $CO_2$ concentration: 5.0%) for four days.

5. Observation of the State of the Cells

After incubating for four days, the state of the cells in the collagen gel was observed under a microscope and the pictures of the representative examples thereof were taken. The results are shown in FIG. 1 and FIG. 2.

6. Measurement of Living Cell Numbers (1) In order to measure the living cell numbers after incubating for four days, each 50 µl of the 1 wt % solution of collagenase was dropped into a well and the mixture was gently stirred together with the well whereupon the collagen gel was dissolved at 37° C. within 30 minutes.

(2) After the collagen gel was dissolved, each 50 µl of an MTT assay solution was added to each well followed by being allowed to stand in an incubator for 30 minutes.

(3) After being allowed to stand for 30 minutes, the absorbance at 450 nm was measured, average value and standard deviation were determined for each collagen gel from the values of the absorbance in eight wells and the result is shown as a graph in FIG. 3. Incidentally, in the graph of FIG. 3, the absorbance of the collagen of the inventive examples is expressed in terms of a relative value where the average absorption of the collagen gels of the comparative examples is defined as 100. In the meanwhile, the absorption is in parallel to the living cell numbers.

7. Consideration of this Experiment (1) Observation of the State of the Cells

As will be apparent from the comparison of FIG. 1 with FIG. 2, the incubation using the collagen of the inventive examples (FIG. 1) shows better growth of the cells than the incubation using the collagen of the comparative examples (FIG. 2) and elongation of the neurite is significant as well.

(2) Measurement of Living Cell Numbers

As will be apparent from FIG. 3, the absorbance of the incubation using the collagen of the inventive examples is higher than the absorbance of the incubation using the collagen of the comparative examples to an extent of 39% in average and the difference as such is a significant difference in view of statistics as well (p<0.01). Accordingly, from the result of FIG. 3, it is noted that the collagen of the inventive examples has the significantly higher cell growth ability than the collagen of the comparative examples.

(3) From the above results, it is concluded that the collagen of the inventive examples is better than the conventional collagen of the comparative examples in terms of the cell growth ability and the differentiation inducing ability.

Experiment 2: Experiment on Adhesive Property of Collagen Coat

1. Object of this Experiment

An object thereof is that, for comparing the cell adhesion property between the collagen of the inventive examples and the conventional collagen, the floating cells after the incubation in both collagens were sucked and removed using an aspirator, only the cells adhered to the plate were measured and their numbers were compared to confirm whether there was a significant difference in the adhesive property of the cells depending upon the type of the collagen.

2. Preparation of Collagen Coat (1) The collagen of the inventive examples and the collagen of the comparative examples were diluted with hydrochloric acid to make the concentration 0.05% by weight and each 300 µl of those collagen solutions was placed into each eight wells of a 24-well microplate (manufactured by Iwaki) followed by being allowed to stand in a refrigerator for one hour.

(2) After being allowed to stand for one hour, the collagen solution in each well was sucked using an aspirator and the collagen coat adhered in the well was subjected to natural drying for 1 hour in a clean bench.

3. Collagen coat incubation of the PC12 cells (1) PC12 cells (cells derived from the adrenal pheochromocytoma of rats manufactured by Dainippon Pharmaceutical Laboratory Products) were previously cultured on a DMEM medium until six passage numbers, the cells were recovered by centrifugal separation and suspended in 25 ml of the DMEM medium so as to adjust the cell numbers to $5 \times 10^6$ cells and then 25 µl of a 50 µg/ml NGF (cell growth factor manufactured by R&D Systems Inc.; a phosphate buffer) was added thereto whereupon a culture solution was prepared.

(2) Each 300 µl of the culture solution prepared as such was dropped into the well of the previously-prepared collagen medium.

(3) The well plate was incubated in an incubator (37° C.; $CO_2$ concentration: 5.0%) for five days.

4. Measurement of Adhered Cell Numbers (1) In order to remove the floating cells and the cells which were not surely adhered, all of the media were sucked by inclining the well plate at an angle of 85°. Careful attention was paid at that time not to suck the adhered cells.

(2) After that, each 300 µl of a DMEM medium and 30 µl of an MTT assay solution were added to each well followed by being allowed to stand in an incubator for 30 minutes.

Figure 4:
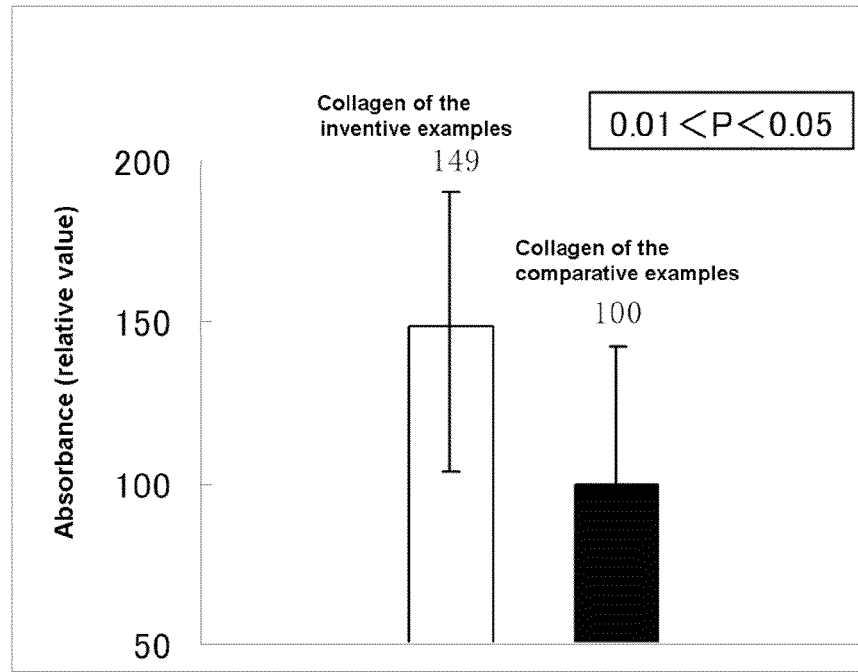
FIG. 4 is a graph of absorption (relative values) measured in Experiment 2.

(3) After being allowed to stand for 30 minutes, the absorbance at 450 nm was measured, average value and standard deviation were determined for each collagen coat from the values of the absorbance in eight wells and the result is shown as a graph in FIG. 4. Incidentally, in the graph of FIG. 4, the absorbance of the collagen coat of the inventive examples is expressed in terms of a relative value where the average absorption of the collagen coat of the comparative examples is defined as 100.

5. Consideration of this Experiment

As will be apparent from FIG. 4, the absorbance which expresses the adhered cell numbers of the collagen coat of the inventive examples was higher than the absorbance of the collagen coat of the comparative examples to an extent of 49% in average and the difference as such was a difference which was significant in terms of statistics as well (0.01<p<0.05). The cell adhesive property is a very important factor for the scaffold in the regeneration medicine and, from the result of FIG. 4, it is noted that the collagen of the present invention is suitable for using as a scaffold for the nerve regeneration as compared with the conventional collagen.

Experiment 3: Collagen Coat Incubation Experiment where Concentration of Sodium Chloride is Changed 1. Object of this Experiment An object thereof is to check the degree of influence of the difference in the concentrations of sodium chloride contained in collagen on the living and the growth of the cells.

2. Preparation of Collagen Coat (1) There were prepared the collagen of the inventive examples used in Experiment 1; that where sodium chloride concentration was made 5% by weight or 10% by weight by addition of sodium chloride thereto; the collagen of the comparative examples used in Experiment 1; and that where sodium chloride concentration was made 5% by weight or 10% by weight by addition of sodium chloride thereto (refer to collagen coats 1 to 6 of FIG. 5). Each of the collagens was made into a 0.01 wt % solution in hydrochloric acid and 300 µl of each collagen was dropped into four wells using two 24-well microplates (manufactured by Iwaki) followed by being allowed to stand in a refrigerator for one hour.

(2) After being allowed to stand for one hour, the collagen solution in each well was sucked using an aspirator and the collagen coat adhered in the well was subjected to natural drying for 1 hour in a clean bench.

3. Collagen Coat Incubation of the PC12 cells (1) PC12 cells (cells derived from the adrenal pheochromocytoma of rats manufactured by Dainippon Pharmaceutical Laboratory Products) were previously cultured on a DMEM medium until six passage numbers, the cells were recovered by centrifugal separation and suspended in 15 ml of the DMEM medium so as to adjust the cell numbers to $1 \times 10^6$ cells and then 15 µl of a 50 µg/ml NGF (cell growth factor manufactured by R&D Systems Inc.; a phosphate buffer) was added thereto whereupon a culture solution was prepared.

(2) Each 300 µl of the culture solution prepared as such was dropped into the well of the previously-prepared collagen medium.

(3) The well plate was incubated in an incubator (37° C.; $CO_2$ concentration: 5.0%) for five days.

4. Measurement of Living Cell Numbers (1) Each 30 µl of an MTT assay solution was added to each well followed by being allowed to stand in an incubator for 30 minutes.

Figure 7:
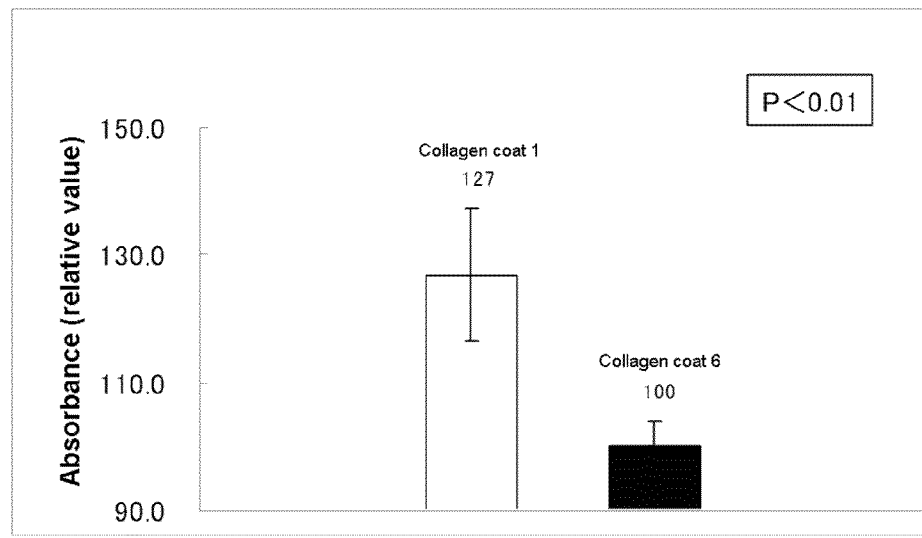
FIG. 7 is a graph of absorption (relative values) measured in Experiment 3.

(2) After being allowed to stand for 30 minutes, the absorbance at 450 nm was measured, average value and standard deviation were determined for each collagen coat from the values of the absorbance in eight wells and the result is shown as graphs in FIGS. 6 and 7. Incidentally, in the graphs of FIGS. 6 and 7, the absorbance of the collagen coat of the inventive examples is expressed in terms of a relative value where the average absorption of the collagen coat of the comparative examples is defined as 100.

5. Consideration of this Experiment

As will be apparent from FIGS. 6 and 7, there is a tendency that the higher the absorbance, the lower the sodium chloride concentration in collagen and the absorbance of the culture using the collagen of the inventive examples (collagen coat 1 (sodium chloride concentration: 1% by weight)) was higher than the absorbance of the culture using the collagen of the comparative examples (collagen coat 6 (sodium chloride concentration: 10% by weight)) to an extent of 27% in average where said difference was a difference which was significant in terms of statistic as well (p<0.01). From the results of FIGS. 6 and 7, it is noted that the collagen of the inventive examples containing low concentration of sodium chloride is superior in the cell growth ability as compared with the collagen of the comparative examples.

Experiment 4: Experiment for evaluating the cell differentiation by incubation of neural crest cells using collagens having different isoelectric points 1. Object of this Experiment An object thereof is to cheek the degree of influence of the difference in the isoelectric points of collagen on the cell differentiation.

2. Preparation of Concentrated Collagen Powder by Means of isoelectric point (1) Milli Q water was added to 6 g of NMP Collagen PS to prepare 1,000 ml, in total, of a 0.6 wt % solution of collagen.

(2) It was stirred on ice for one to three day (s) so that the collagen was completely dissolved in water.

(3) 1N NaOH was dropped thereinto and 200 ml of a collagen solution containing the precipitate in a state of pH 5.5 was recovered to another container.

(4) Dropping of 1N NaOH was continued and, similarly, each 200 ml solution in a state of pH 8.5 and 10.2 was recovered to another container.

(5) Each of the resulting three samples were transferred to a centrifugal tube and centrifuged at 3,000 rpm for 45 minutes.

(6) Supernatant liquid in each centrifugal tube was discarded and the precipitate was frozen at −40° C. through the night and treated for two days in a freeze-drying machine.

(7) The resulting samples were called a sample 1 (pH 5.5), a sample 2 (pH 8.5) and a sample 3 (pH 10.2) successively.

In each of the collagen samples, concentration of sodium chloride was 1.2% by weight.

3. Preparation of collagen solution (1) To each 300 mg of the above samples 1, 2 and 3 was added 0.001M HCl to prepare 10 ml, in total, of a 0.3 wt % collagen solution.

(2) Mixing was conducted using Voltex followed by being allowed to stand at 4° C. through the night so that collagen was completely dissolved.

(3) To each 1 ml of the sample of 0.3 wt % concentration was added 9 ml of 0.001M HCl followed by well mixing to prepare a 0.03 wt % collagen solution.

(4) Each 200 µl of the above 0.03 wt % collagen solution was placed in each well of a 24-well microplate (manufactured by Iwaki) followed by being allowed to stand at room temperature (20° C.) for ten minutes.

(5) The collagen solution was sucked, 1 ml of PBS(−) was added thereto and the mixture was sucked, washed and repeatedly washed.

(6) The above was just allowed to stand in a clean bench to dry.

4. Incubation of the Cells

Pigment cells derived from neural crest (manufactured by Kurabo Industries; Code No. KM-4009MP) was diluted with a medium exclusively therefor (manufactured by Kurabo Industries; Code No. M-254-500+Code No. S-002-5) to make $3.75 \times 10^4$ cells per ml and then 500 µl thereof was sown onto each well.

(2) Incubation was conducted for four days at 37° C. where $CO_2$ concentration was 5.0%.

(3) After sucking the medium, 500 µl of the exclusive medium was freshly added thereto and, after that, incubation was conducted for three days at 37° C. where $CO_2$ concentration was 5.0%.

(4) After sucking the medium, 500 µl of the exclusive medium was freshly added thereto, incubation was conducted for four days more at 37° C. where $CO_2$ concentration was 5.0% and, after that, degree of cell differentiation in each well was observed.

5. Consideration of this Experiment

Figure 8:
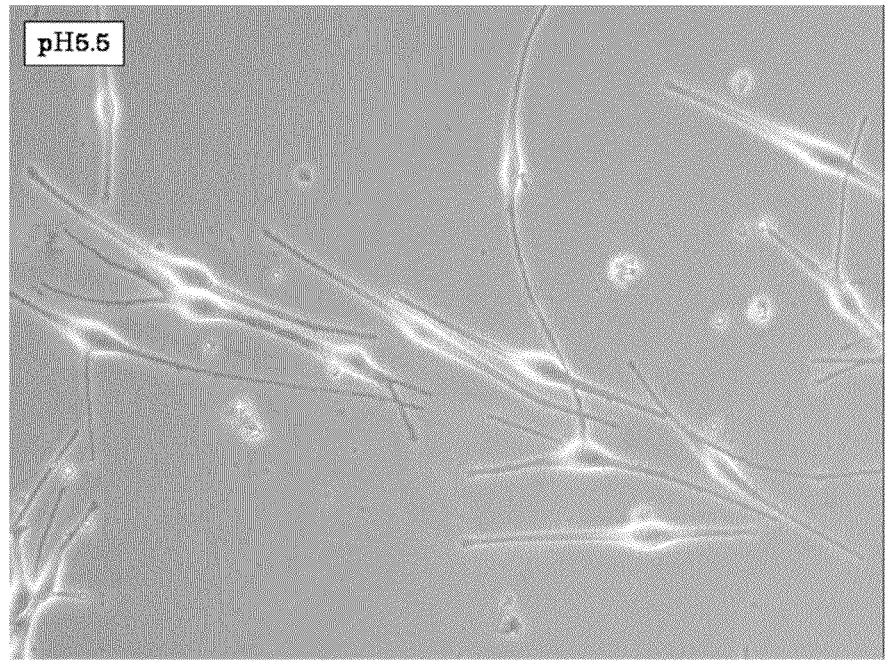
FIG. 8 is a microscopic picture showing the state of cell differentiation cultured on a collagen (pH 5.5) coat plate of Experiment 4.
Figure 9:
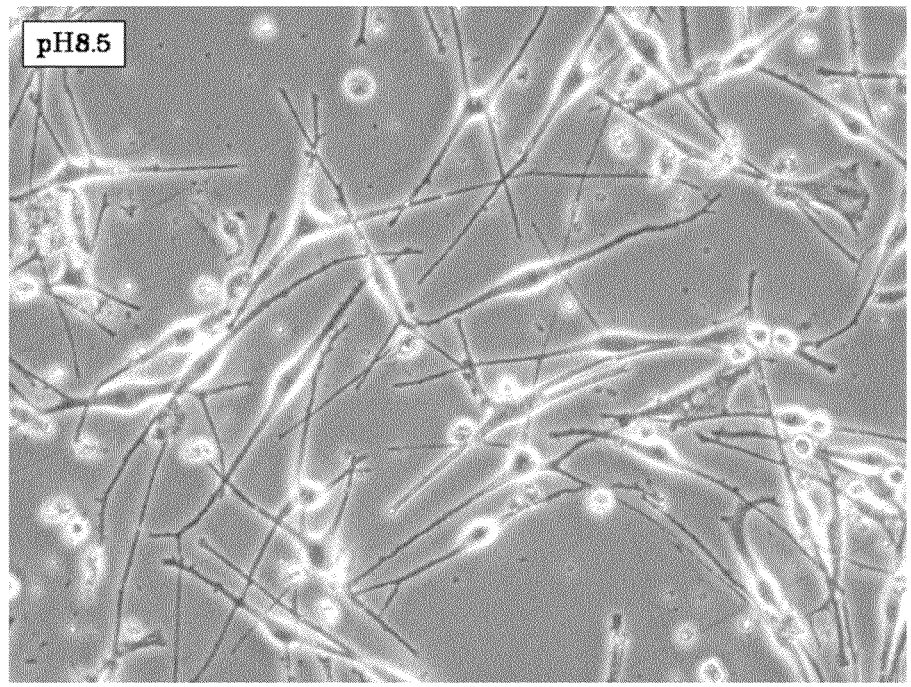
FIG. 9 is a microscopic picture showing the state of cell differentiation cultured on a collagen (pH 8.5) coat plate of Experiment 4.
Figure 10:
FIG. 10 is a microscopic picture showing the state of cell differentiation cultured on a collagen (pH 10.2) coat plate of Experiment 4.

As will be apparent from FIGS. 8 to 10, significant differences were noted in the cell differentiation levels depending upon the difference in the isoelectric point of collagen and it could be confirmed from the observation of the cell form that the differentiation was significantly promoted in the sample 2 (pH 8.5).

Figure 11:
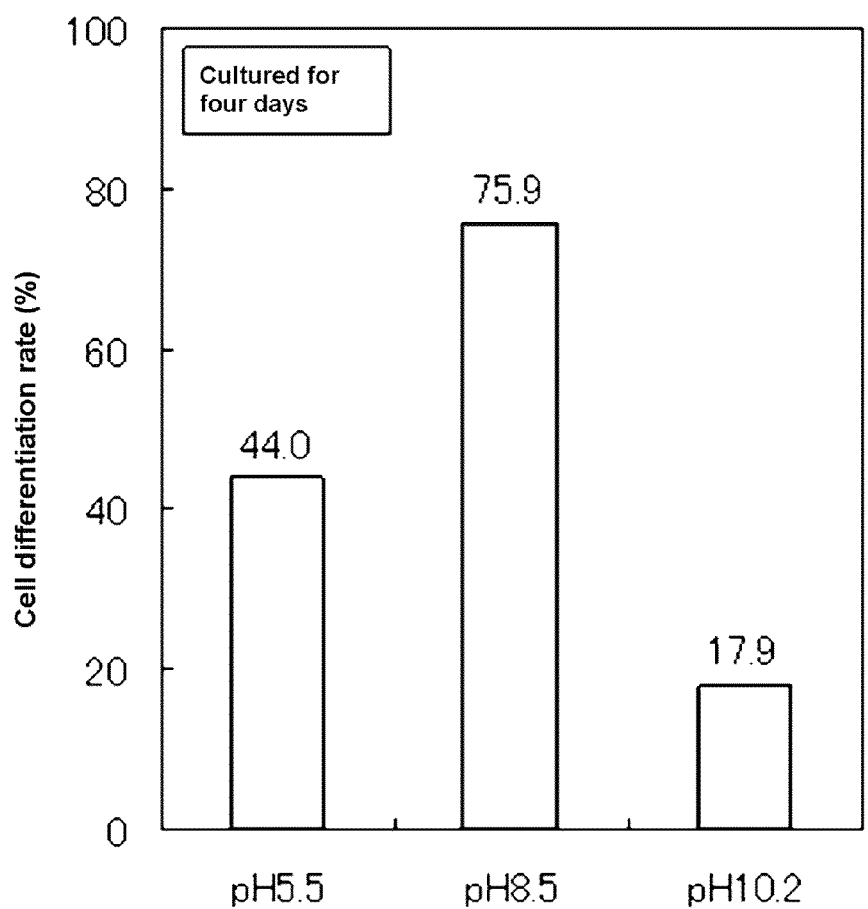
FIG. 11 is a graph of the cell differentiation rate after culturing for four days measured in Experiment 4.
Figure 12:
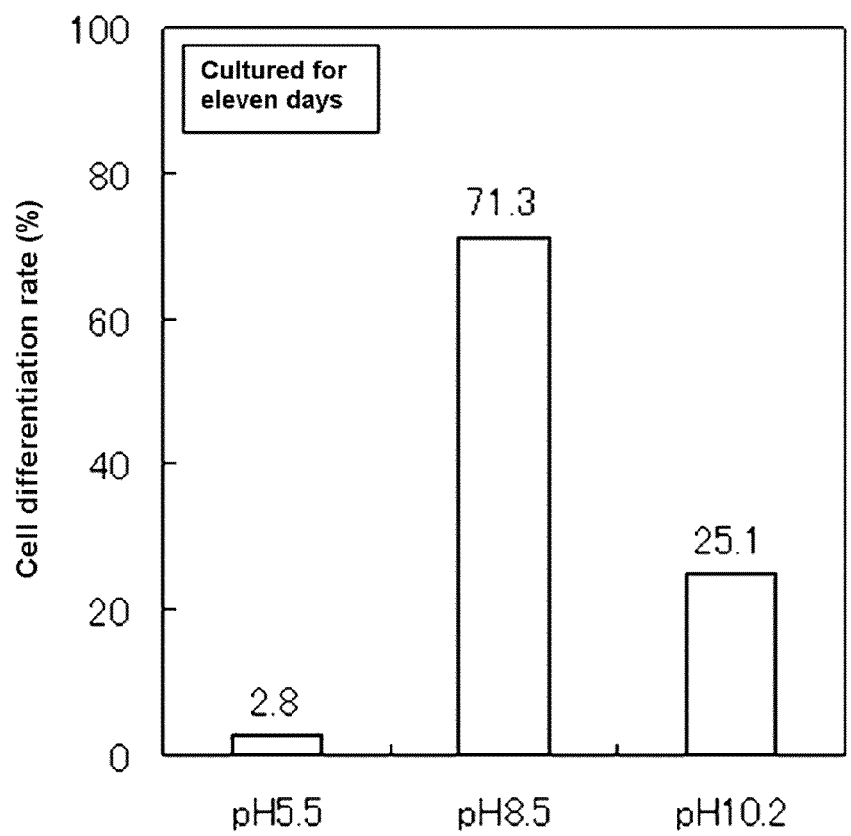
FIG. 12 is a graph of the cell differentiation rate after culturing for eleven days measured in Experiment 4.

It was further confirmed from FIGS. 11 and 12 that, when the rate of the differentiated cells in the total living cells was calculated, the cell differentiation rate (%) was high when pH was 8.5 as compared with the cases where pH was 5.5 and 10.2.

Cell differentiation rate(%)=(Differentiated cell numbers)/(Total living cell numbers)

In view of the fact that, in general, collagen is metabolized/absorbed in vivo within about two weeks, it is believed that, if 40% or more cell differentiation rate is available after the incubation for 11 days, good result is achieved in the actual field of nerve regeneration. The cell differentiation rate is more preferably not less than 50%, more preferably not less than 60%, and more preferably not less than 70%.

INDUSTRIAL APPLICABILITY

Since the nerve regeneration-inducing tube according to the present invention is excellent in terms of cell adhesion property, cell growth ability and cell differentiation inducing ability, its application in the nerve regeneration medicine is expanded and it is quite useful.

The invention claimed is:

1. A nerve regeneration-inducing tube, comprising:
a tubular body comprising a biodegradable polymer, and
collagen coated on said tubular body and filled into said tubular body as a scaffold for nerve regeneration,
wherein a concentration of sodium chloride relative to said collagen is not more than 2.0% by weight in a dry state, and
wherein said collagen coated on said tubular body and filled into said tubular body consists essentially of at least one of type I and type III collagen.

2. The nerve regeneration-inducing tube according to claim 1, wherein the collagen is purified by means of an isoelectric precipitation where the pH is 6.0 or higher and is lower than 10.0.

3. The nerve regeneration-inducing tube according to claim 1, wherein the concentration of sodium chloride relative to said collagen is 0.1 to 1.5% by weight in the dry state.

4. The nerve regeneration-inducing tube according to claim 2, wherein the concentration of sodium chloride relative to said collagen is 0.1 to 1.5% by weight in the dry state.

* * * * *